US005558836A

United States Patent [19]
Rounbehler et al.

[11] Patent Number: 5,558,836
[45] Date of Patent: Sep. 24, 1996

[54] EMISSION DETECTION SYSTEMS FOR DETERMINING THE PRESENCE OF CONTAMINANTS

[75] Inventors: David P. Rounbehler, Bedford; Dirk Appel, Salem; Daniel A. Dussault, Newburyport, all of Mass.; Thomas M. Levine, Lee, N.H.; Jonathan E. Bosworth, Acton, Mass.

[73] Assignee: Thermedics Detection Inc., Woburn, Mass.

[21] Appl. No.: 316,905

[22] Filed: Oct. 3, 1994

[51] Int. Cl.$^6$ .................................................. G01N 21/15
[52] U.S. Cl. .................. 422/91; 436/172; 356/218; 356/437; 73/23.37; 73/23.42; 73/31.03; 73/31.05
[58] Field of Search .................. 42/91, 82.08; 436/140, 436/172, 52, 53; 73/23.4, 23.42, 23.37, 31.03, 31.05; 356/437, 442, 218

[56] References Cited

U.S. PATENT DOCUMENTS

| | | | |
|---|---|---|---|
| 3,845,309 | 10/1974 | Helm et al. | 356/240 |
| 3,932,042 | 6/1976 | Fanni et al. | 356/240 |
| 3,970,430 | 7/1976 | Reader, Jr. et al. | 422/83 |
| 4,221,961 | 9/1980 | Peyton | 250/223 |
| 4,272,248 | 6/1981 | Neti | 436/122 |
| 4,998,824 | 3/1991 | Littlejohn et al. | 356/407 |
| 5,002,397 | 3/1991 | Ingrum et al. | 356/407 |
| 5,083,865 | 1/1992 | Kinney et al. | 356/338 |
| 5,108,705 | 4/1992 | Rounbehler et al. | 422/91 |
| 5,318,911 | 6/1994 | Fine et al. | 209/3.1 |
| 5,330,714 | 7/1994 | Godec et al. | 422/82.08 |

OTHER PUBLICATIONS

Thermo Environmental Instruments Inc. Specification Sheet, Transmissometer—Model 400 and 400B.
Thermo Environmental Instruments Inc. Specification Sheet, Ultrasonic Stack Gas Flow Meter—Model 220.
Thermo Environmental Instruments Inc. Specification Sheet, Gas Emissions Monitor—Model 100.
Thermo Environmental Instruments Inc. Specification Sheet, Pulsed Fluorescence $SO_2$ Analyzer—Model 43A.

Primary Examiner—James C. Housel
Assistant Examiner—Rachel Heather Freed
Attorney, Agent, or Firm—Fish & Richardson P.C.

[57] ABSTRACT

A detection system for detecting the emission (i.e., the fluorescence or phosphorescence) from a contaminant contained in a sample gas. In order to keep the optics of the system clean and maintain a high signal-to-noise ratio in the detected signal, the detection system contains a housing separated into illumination and sample chambers by an aperture-containing partition. A sample inlet port is connected to the sample chamber, and a purge inlet port is connected to the illumination chamber to direct the purge and sample gasses into their respective chambers. A vacuum system is connected to a vacuum port on the sample chamber to simultaneously draw the sample and purge gasses into their chambers through the inlet ports; the purge gas is then drawn through the aperture and into the sample chamber. Finally, both gasses are drawn out of the sample chamber through the vacuum port. Thus, the vacuum provides a flow of sample gas into the sample chamber, and a flow of purge gas into the illumination chamber to reduce contact between the sample gas and a portion of the optics, thereby keeping them free of debris.

17 Claims, 3 Drawing Sheets 5,558,836

EMISSION DETECTION SYSTEMS FOR DETERMINING THE PRESENCE OF CONTAMINANTS

BACKGROUND

This invention relates to optical detection systems, particularly those used to measure contaminants present in refillable bottles.

The popularity of refillable containers (typically composed of glass or polymeric materials, e.g., polyethylene terephthalate) has increased, in part due to the environmental and financial costs associated with disposal of containers. After use, refillable containers may be returned to a bottling plant for cleaning and inspection before being refilled. This inspection screens the containers for physical damage (e.g., cracking) and contaminants (e.g., hydrocarbons and detergents) that might degrade the flavor, safety, or other qualities of the final product. The risk of contamination is particularly high in containers made from plastic, rather than glass, because contaminants tend to absorb into the plastic walls of the container, and may leach into the product despite cleaning procedures.

It is usually desirable, therefore, to test the container for trace amounts of contaminants prior to refilling. Such tests are preferably rapid and non-invasive in order to be efficiently incorporated into high-volume refilling processes involving assembly lines.

An existing contaminant-testing method involves the use of a gas nozzle configured to deliver pressurized air or another suitable gas to the containers, thereby displacing a portion of the gas-phase contaminants contained within. The displaced contaminants are then imported as a sample to one or more detectors, such as an optical excitation/detection mechanism, positioned at a point away from the point of samplings. Such systems are used to optically monitor the presence of the contaminants, and typically include a light source (e.g., a laser or flashlamp) which is used to optically excite the gas-phase contaminants in the sample. As the excited molecular components of the contaminants return to their ground states, they emit a characteristic fluorescence with an intensity linearly proportional to their concentration. The induced fluorescence is then imaged onto a photodetector using a lens or an equivalent optical system.

When such a system is used to detect trace amounts of contaminants, it is usually desirable to maximize the signal-to-noise ratio of the detected signal. Unfortunately, dust or contaminants continuously drawn into the housing containing the excitation/detection system may collect on the various optical components (particularly on glass-based components, such as lenses and mirrors), causing attenuation of the detected signal. Filtration of the sample to remove debris is typically impractical as this process may also remove the contaminant to be detected. Additionally, the presence of debris tends to increase the magnitude of the diffuse scattered excitation light, which in turn increases the amount of detected noise. When the build-up of these foreign materials is such that an adequate signal-to-noise ratio in the measured signal cannot be achieved, the assembly line must be stopped in order for the optical components to be cleaned; this process is undesirably frequent when such fluorescence detectors are used in dirty environments.

SUMMARY

In general, in one aspect, the invention provides a detection system for detecting the emission (i.e., the fluorescence or phosphorescence) from a contaminant contained in a sample gas. The detection system includes a housing containing sample and purge inlet ports for directing, respectively, the purge and sample gasses into the housing, and a vacuum port configured to direct both the sample and purge gases out of the housing. A light source and a first optical system are used for providing a beam of radiation at an orientation, wavelength, and intensity sufficient to irradiate and induce emission in the contaminant contained in the sample gas directed into the housing; the emission is then detected with a photodetector positioned with respect to the housing so as to generate a light-induced signal characteristic of the contaminant. A purge gas flow path is defined in the housing from the purge inlet port past at least a portion of the first optical system. A vacuum system is connected to the vacuum port to simultaneously draw the sample and purge gasses into the housing through, respectively, the sample and purge inlet ports, and then out of the housing through the vacuum port. This provides a flow of sample gas into the sample chamber, and a flow of purge gas, along the purge gas flow path, and into the housing to reduce contact between the sample gas and a portion of the first optical system. A processor is also included in the emission detection system for analyzing the light-induced signal to determine the presence of the contaminant.

In preferred embodiments, the housing of the detection system further includes a partition containing an aperture. The partition is positioned within the housing to form (a) an illumination chamber containing a portion of the optical system; and, (b) a sample chamber containing the flowing gas sample. In this case, the sample inlet port is configured to direct the sample gas directly into the sample chamber, and the purge inlet port is configured to direct the purge gas directly into the illumination chamber. Preferably, the vacuum port is connected to the sample chamber.

In such embodiments, the aperture is positioned to allow the purge gas to flow from the illumination chamber to the sample chamber in response to the vacuum. The first optical system, which preferably contains a lens or a transparent window, may also be aligned to direct optical radiation through the aperture to irradiate the gas sample in the sample chamber. In addition, the aperture may be configured to spatially filter the optical radiation to improve the spatial intensity profile of the beam. The photodetector used to detect the emission is preferably positioned substantially orthogonal to the path of the beam.

In still other embodiments, in order to direct the purge gas into the housing, the emission detection system contains a purging system connected to the purge inlet port. The purging system may include (separately or in combination) a capillary tube for directing the purge gas into the housing; an isolated source of a gas (i.e., air, nitrogen, or argon) attached to the capillary tube; a filter to allow filtering of the purge gas before it enters the housing; and, a valve for controlling the flow of the purge gas.

In another aspect, the invention provides a method of reducing the build-up of debris from a contaminant-containing sample gas on a portion of an optical delivery system contained within the housing of an emission-detecting system. The method includes the step of dividing the housing into a sample chamber containing a sample inlet port and a vacuum port, and an illumination chamber containing a portion of the optical delivery system and a purge inlet port. This allows the sample and illumination chambers to be in gaseous communication with each other through an aperture. An exhausting step partially evacuates the sample chamber so as to (a) draw purge gas into the illumination chamber, through the purge inlet port, and out through the aperture into the sample chamber; (b) draw sample gas into the sample chamber through the sample inlet port; and, (c) draw both the sample and purge gas out of the sample chamber and through the vacuum port. The exhausting and dividing steps, in combination, reduce the build-up of debris on the optics by keeping portions of the illumination chamber continuously flooded with purge gas and reducing the contact between the sample gas and the optics.

Accordingly, by reducing the amount of contaminant (and other debris) which may collect on the optics of the system, the present invention allows the magnitude of the background signal to be reduced, and the sensitivity of the contaminant-detecting system to be increased. In addition, scattered excitation light which may excite other fluorescing materials not contained in the sample, i.e, foreign material which has accumulated on the inner walls of the excitation chamber, is reduced using the vacuum gas purge and the aperture. Incorporation of the aperture and purge gas decreases the level of background light not attributed to the sample emission (i.e., the noise). Thus, the signal-to-noise ratio of the detected signal is increased, allowing the sensitivity of the detector to be increased. Because the optics are kept clean, the detection system can operate for long periods of time without interruption.

As used herein, "contaminant" is meant a substance that can be detected in a container, and whose presence is incompatible with the product with which the container is to be filled. For example, gaseous hydrocarbons (particularly aromatic hydrocarbons), detergents, and $SO_2$ are contaminants which can be detected in beverage containers.

DETAILED DESCRIPTION OF THE PREFERRED EMBODIMENTS

Figure 1:
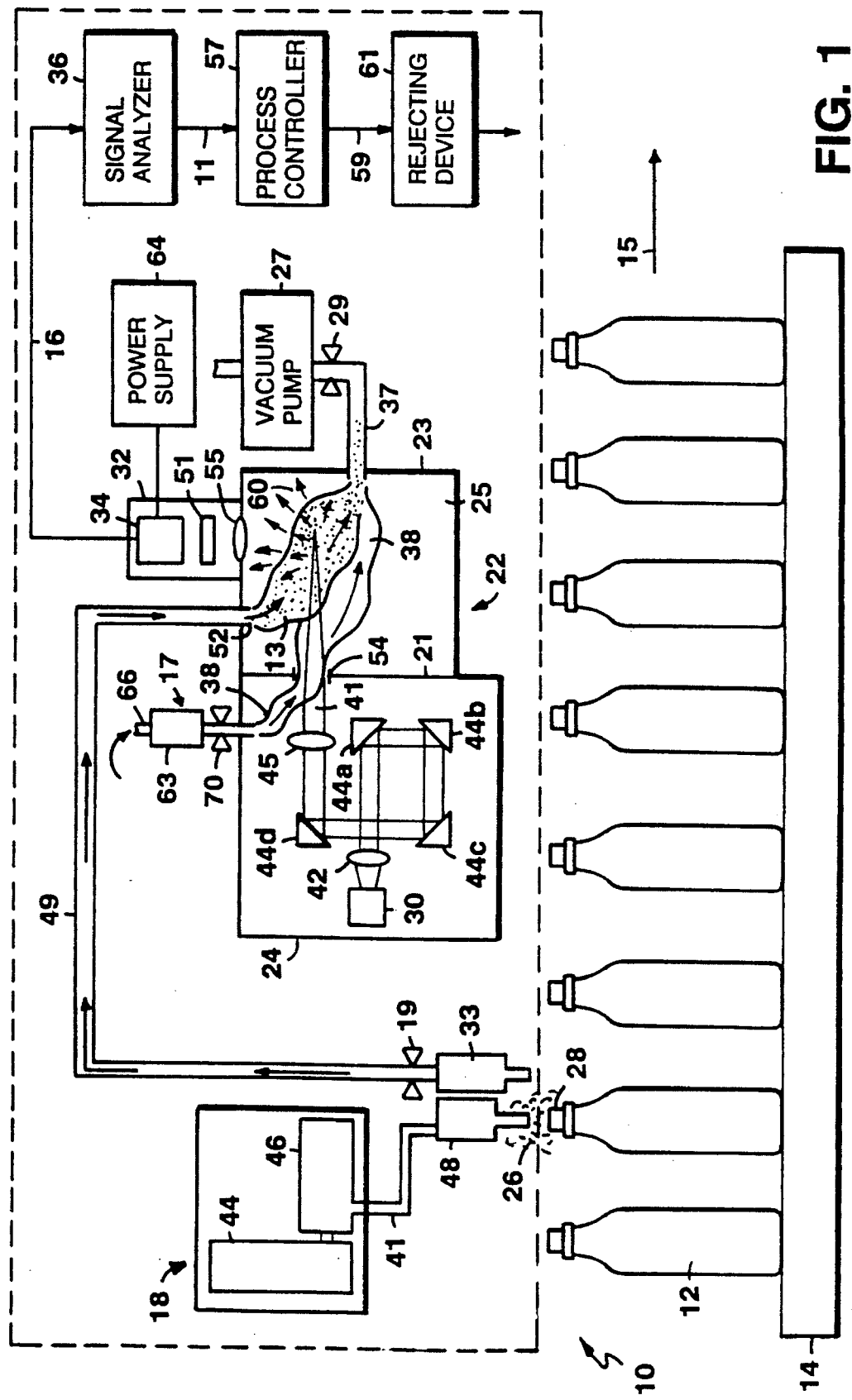
FIG. 1 is a side schematic view of a refillable bottling assembly line equipped with a gas sampling system and a fluorescence detection system according to the invention.
Figure 2:
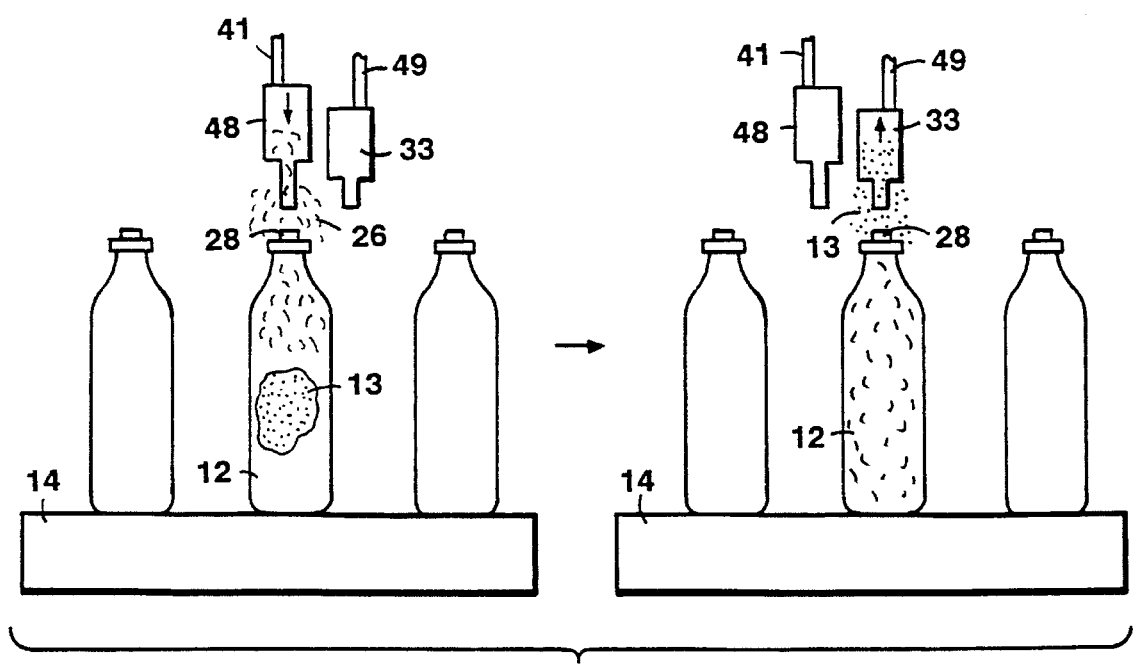
FIG. 2 consists of two similar side schematic views of the gas sampling system of FIG. 1 showing bottles encountering jet and suction nozzles (left and right, respectively, as shown).

With reference to FIGS. 1 and 2, a contaminant detection system 10 used to detect specific contaminants such as aromatic hydrocarbons (e.g., compounds in gasoline) present in refillable containers 12 moving in a direction indicated by an arrow 15 along an assembly line 14 (e.g., a conveyor) includes a nozzle system 18 for displacing contaminant-containing gas from the container, and a excitation/detection system 22 which allows small amounts of contaminants to be accurately detected. The excitation/detection system 22 is positioned with respect to the assembly line 14 so that, during operation, a gas-phase contaminant 13 present in any container moving along the assembly line 14 can be rapidly and non-invasively detected in a sample acquired from the container 12.

Once a sample has been delivered to the excitation/detection system 22, the presence of a contaminant is detected using optical methods. In particular, when exposed to a radiation beam 41 from a light source 30, emission 60 from optically active contaminants can be detected in small quantities using a photodetector 34. This device generates a light-induced electrical signal which is directed along line 16 for analysis by a signal analyzer 36, such as a computer. If the signal indicates that a bottle is contaminated, a second signal is sent along line 11 to a process controller 57, which sends a "reject" signal along line 59 to a rejecting device 61, which then removes the contaminated bottle from the assembly line. Such a rejecting device, for example, is described in U.S. Ser. No. 08/023,327, filed Feb. 26, 1993 by Fine et al., entitled "Rejector System for Conveyor Line", the contents of which are incorporated herein by reference.

Detection of small amounts of the gas-phase contaminant 13 requires the light-induced signal produced by the photodetector 34 to have a high signal-to-noise ratio. In particular, during operation, it is desirable to reduce the accumulation of dust, foam, contaminants, or any other material on the optical components of the detection system. The present invention incorporates a gas-purging mechanism 17 which allows a gas flow 38, or "air curtain", to be suctioned into the excitation/detection system 22, thereby reducing the accumulation of debris in the system and allowing the optics to be kept clean and highly transmissive or reflective. In addition, an aperture 54 contained in a partition 21 separating the illuminating 24 and excitation 25 chambers further prevents contact between the optics and material introduced to the detection system 22. The aperture may also spatially filter the beam, thereby removing excess scatter. The combination of the aperture and gas purge mechanisms allows a high level of light to be delivered to the sample of interest, and reduces the amount of scattered excitation light which may illuminate optically active contaminants accumulating on the walls or optical components of the excitation chamber 25 over time. Ultimately, this results in detection of a high level of the induced fluorescence (i.e., the signal) and a low level of the amount of scatter-induced fluorescence background (i.e., the noise). Thus, the signal-to-noise ratio of the detected signal remains high over time, allowing small amounts of contaminants to be accurately measured.

In order to transport the gas-phase contaminant 13 from the container 12 to the optical contaminant system 22, a high-pressure flow of gas 26 (e.g., air or nitrogen) is delivered, either in pulses (see FIG. 2) or continuously, from a gas supply 44 to a nozzle 48, and then into the open mouth 28 of each container 12. The gas 26 displaces gases and vapors, including the gas-phase contaminant 13 (if present), from the container 12 to form a sample "cloud" just above the open mouth 28. Alternatively, if the contaminant is present in the liquid phase, the burst of gas 26 serves to evaporate or aerosolize a portion of the contaminant, thereby driving small amounts of this material into the gas-phase. Typically, the gas supply 44 is connected by way of a pump 46 and a pipe network 41 (which may include a filter) to the nozzle 48, which is positioned directly above the openings 28 of the containers 12 moving along the assembly line. If the nozzle 48 is pulsed, the arrival of the burst of gas 26 is synchronized (and in phase) with the arrival of containers 12 moving along the assembly line. Preferably, the nozzle 48 and suction nozzle 33 operate continuously, particularly when container speeds are high, e.g., up to 450 containers per minute or higher.

Once displaced (or driven to the gas phase) to form part of a cloud above the container 12, the gas-phase contaminant 13 is suctioned off in a sample from the cloud by a second nozzle 33, which is adjacent to nozzle 48 and is attached via a vacuum pipe network 49 to the optical excitation/detection system 22. This system is placed under partial vacuum using a pump 27 and a control valve 29 connected to a vacuum line 37. The rate at which the sample is suctioned off is determined by the vacuum and an adjustable control valve 19; a sample inlet port 52 allows delivery of the sample into the optical contaminant system 22. Nozzle systems of this kind have been described, for example, in Fine et al., U.S. Pat. No. 5,318,911, issued Jun. 7, 1994, entitled "System for Sampling and Determining the Presence of Compounds in Containers" the contents of which are incorporated herein by reference. Fluorescence detectors of the general type described below, but without the purge and spatial-filtering improvements, are described in Helm et al., U.S. Pat. No. 3,845,309, issued Oct. 29, 1974, entitled "Fluorescent Gas Analyzer", the contents of which are also incorporated herein by reference.

Figure 3A:
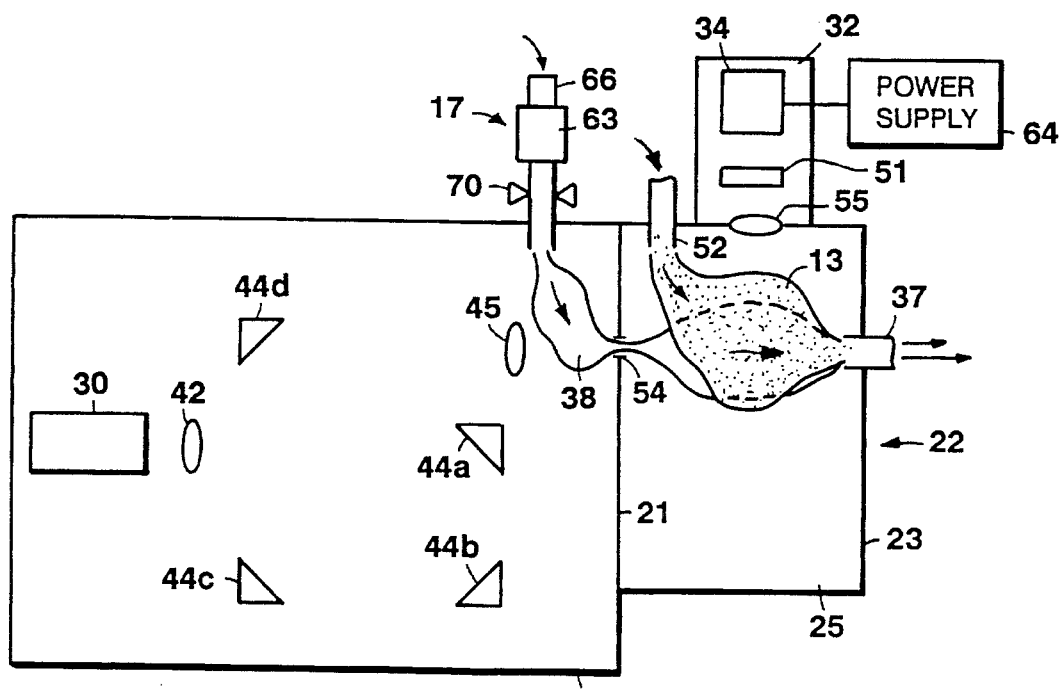
FIGS. 3A and 3B are side schematic views of the fluorescence detection system showing, respectively, the purge gas and the optical excitation beam interacting with the sample.
Figure 3B:
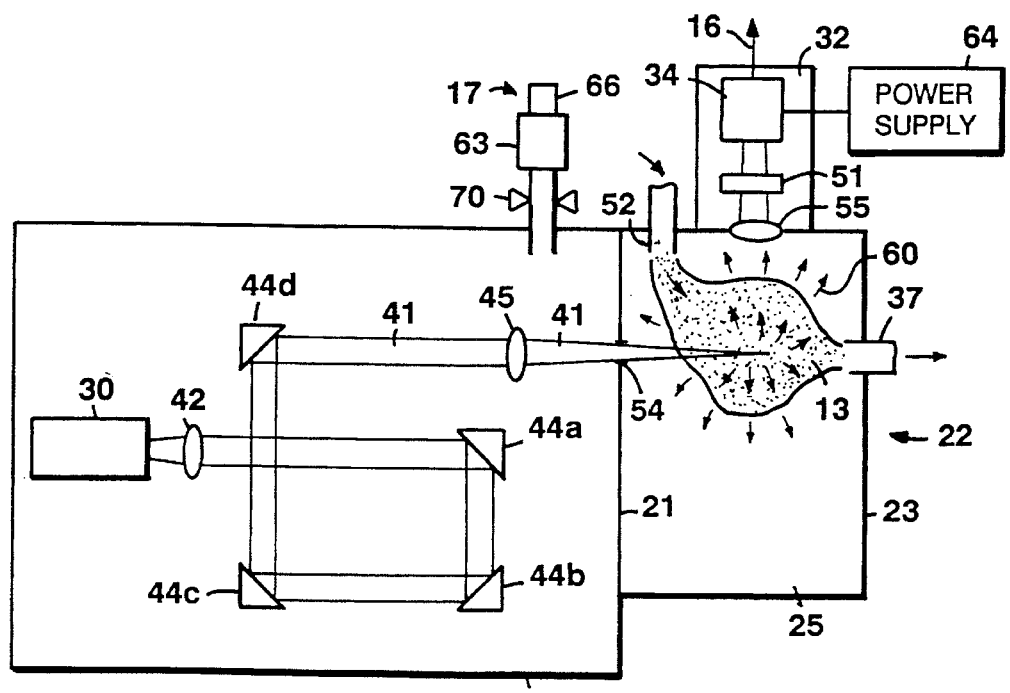

With reference now to FIGS. 1, 3A, and 3B, the optical contaminant system 22 includes a first housing forming a detection chamber 32 which houses the optical/electronic devices used for light detection, and a second housing 23 defining the illumination chamber 24 and the excitation chamber 25. These two chambers are separated by a partition 21 containing the aperture 54. The illumination chamber 24 contains a first optical system for delivering the beam 41 from the light source 30 to the sample, and the excitation chamber 25 contains a second optical system including a lens 55 to image emitted light 60 through a bandpass filter 51 and onto a photodetector 34 within the detection chamber 32.

With reference now to FIGS. 1 and 3A (wherein the beam 41 is omitted), vacuum applied to the vacuum line 37 by the pump 27 draws a sample containing the gas-phase contaminant 13 into the excitation chamber 25 so that it passes in front of the detection chamber 32. The vacuum also draws a stream of purge gas 38 through a capillary tube 66 and into the illumination chamber 24. Before entering, the purge gas 38 passes through a filter 63 attached to the capillary tube 66, thereby providing a clean, positive flow of gas. A valve 70 is used to controllably adjust the flow of gas, which is typically air, to an optimum level, which is typically in the range of about 8 to 16 liters/minute. After entering the illumination chamber 24, the purge gas is drawn into the excitation chamber 25 through the aperture 54 included on the partition 21. By positioning the contaminant flow downstream from the purge gas, the air curtain prevents the accumulation of the gaseous contaminant 13 and other debris on a series of reflective band-pass filters 44a–44d and lenses 42 and 45 used to deliver the light to the sample. The purge gas, in combination with the aperture, is particularly effective in keeping the lens 45 free of debris; by maintaining the transmissivity of this optic at a high level, the excitation of contaminants on the lens and scatter in the excitation beam, both of which may ultimately induce background noise in the signal, are reduced. In addition, the air purge helps keep the inner surfaces of the illumination chamber 24 relatively clean. After passing through the excitation chamber, both the gaseous contaminant 13 and the purge gas 38 are evacuated through the vacuum line 37 attached to the sample chamber 25.

With reference now to FIG. 3B (wherein the purge gas 38 is not shown), emission 60 is induced in the gas-phase contaminant 13 using a beam 41 generated by a light source 30, which may be, e.g., a laser or a broad-band flashlamp. Preferably, the light source 30 is a pulsed xenon flashlamp (operating, e.g., at 80 Hz), and the lens 42 is used for collimating the beam 41 from the source 30. Depending on the nature of the emitted beam, the lens may be convex or concave; preferably, the lens is plano-convex, and has a focal length of between 5 and 30 cm. Once the beam is collimated, the series of reflective bandpass filters 44a–44d are used to steer the beam 41 through the focussing lens 45, which typically has a focal length of between 4 and 15 cm. Although the light source 30 is shown as positioned within the illumination chamber 24, it may be located external to the housing 23. For example, prior to being delivered to the collimating lens 42, the beam 41 produced by the light source 30 may be first coupled into an optical waveguide, such as a single optical fiber or a fiber optic bundle, thereby allowing the light to be delivered from a remote light source to the excitation/detection system 22. Alternatively, the focussing lens 45 can be mounted in a wall of the illumination chamber so that only the front surface of the final optical element is exposed to the illumination chamber. Similarly, the positions of the delivery optics within the housing may be adjusted for different optical configurations.

The light source 30 and the set of reflective bandpass filters 44a–44d are chosen so that radiation directed at samples within the excitation chamber 25 is absorbed by the gas-phase contaminants, thereby promoting these molecules into their emitting excited states. Preferably, for aromatic hydrocarbon contaminants, these wavelengths are in the ultraviolet spectral region (i.e., less than 400 nm and typically about 200 to 230 nm). The excitation field may be continuous in nature, pulsed, or modulated (i.e., chopped at a set frequency) so that the optical excitation is synchronized with the arrival of the contaminant-containing sample gas 13.

Prior to entering the excitation chamber 25, the beam 41 is focussed through the aperture 54 positioned on the partition 21. The aperture 54 thus provides a "spatial filter" for the beam 41, which improves its spatial intensity profile by reducing unwanted scattered light, or, in some cases, further collimating the beam. In addition, by spatially blocking the flow of the contaminant and dust into the illumination chamber 24, the partition 21 and aperture 54 further reduce the accumulation of debris on the collimating and focussing lenses 42, 45 and on the reflective bandpass filters 44a–44d, thereby increasing the transmissivity and reflectivity of these optics. After passing through the aperture 54, the beam enters the excitation chamber 25, where it is used to optically excite the contaminants in the gaseous sample entering through the sample inlet port 52. If the lens 45 is used to focus the beam 41, it is preferable that the focal plane of the beam interact with the gaseous contaminant directly in front of a collection lens 55.

Following absorption of the excitation field, the contaminants emit light 60 at a wavelength typically between 250 and 700 nm. The emission is then imaged by the lens 55, through a bandpass filter 51, and onto a photodetector 34 connected to a power supply 64. The photodetector may be a photomultiplier tube, a diode array, an optical multichannel analyzer, or any other suitable detector configured to provide a light-induced signal characteristic of the contaminant. The bandpass filter 51 absorbs (or reflects) the excitation light, and transmits a portion of the emitted light, which is between wavelengths of about 300 to 340 nm for substances such as aromatic hydrocarbons. In addition, electronics allowing phase-sensitive detection, such as lock-in amplifiers, or current amplifiers, may be used in combination with the photodetectors to amplify the light-induced signal and further filter out unwanted noise. The illumination, excitation, and detection chambers 24, 25, and 32 are light-tight, with their inner surfaces painted matte black to minimize the amount of reflected and scattered light.

The invention may be in the form of other embodiments. For example, the light source included in the optical detection system may be used to directly irradiate the contaminant, or may only pass through a transparent window before irradiation, thereby eliminating the need for the beam-steering (e.g., reflective bandpass filters) and focussing optics shown in FIGS. 1, 3A, and 3B. Similarly, in another variation, beam-steering or other optics may be used to direct the emission into the photodetector. Alternatively, a fiber optic device, such as a single fiber or a fiber optic bundle, may be used to deliver light to the photodetector. If desired, in addition to the vacuum applied to the housing, the purge gas line can be pressurized to supply purge gas under pressure to the illumination chamber, thereby increasing the pressure difference between the two chambers. However, it has been found that drawing the purge gas into the illumination chamber by exhausting the excitation chamber causes sufficient positive flow of purge gas through the aperture to keep the sample gas out of the illumination chamber.

Other embodiments are within the scope of the following claims.

What is claimed is:

1. A detection system for detecting the emission from a contaminant contained in a sample gas, said detection system comprising:

a housing containing a sample inlet port and a purge inlet port for independently directing the purge and sample gasses into said housing, and a vacuum port configured to direct both the sample and purge gases out of said housing;

a partition containing an aperture positioned within said housing;

a light source and a first optical system positioned within said housing and for providing a beam of radiation at an orientation, wavelength, and intensity sufficient to pass through said aperture and irradiate the sample gas directed into said housing, thereby inducing emission in the contaminant whereby the beam of radiation passes through said aperture prior to irradiation of the sample;

a purge gas flow path defined in said housing from said purge inlet port past said first optical system;

a photodetector positioned with respect to said housing so as to generate a light-induced signal in response to the emission from the contaminant;

a vacuum system connected to said vacuum port to draw: a) the sample gas into said housing through said sample inlet port, and then out of said housing through said vacuum port; and, b) the purge gas into said housing, from said purge inlet through said aperture, and then out of said housing through said vacuum port, thereby providing in said housing a flow of sample gas to be irradiated by said light source and said first optical system, and said purge gas flow path to reduce contact between the sample gas and said first optical system; and a processor for analyzing the light-induced signal to determine the presence of the contaminant.

2. The detection system of claim 1, wherein said partition is positioned within said housing to form an illumination chamber containing said first optical system; and a sample chamber containing said flow of sample gas.

3. The detection system of claim 2, wherein said sample inlet port is configured to direct the sample gas directly into said sample chamber, and said purge inlet port is configured to direct the purge gas directly into said illumination chamber.

4. The detection system of claim 3, wherein said vacuum port is connected to said sample chamber.

5. The detection system of claim 4, wherein said aperture is positioned to allow the purge gas to flow from said illumination chamber to said sample chamber in response to a vacuum.

6. The detection system of claim 1, wherein said first optical system is aligned to direct said beam of radiation through said aperture to irradiate the gas sample in said sample chamber.

7. The detection system of claim 6, wherein said aperture is configured to spatially filter said beam of radiation.

8. The detection system of claim 7, wherein said aperture has an area of between 0.01 and 1 $cm^2$, inclusive.

9. The detection system of claim 1, wherein a purging system is connected to said purge inlet port to direct the purge gas through said purge inlet port and into said housing.

10. The detection system of claim 9, wherein said purging system comprises a capillary tube for directing the purge gas into said housing.

11. The detection system of claim 10, wherein said purging system further comprises an isolated source of a gas attached to said capillary tube.

12. The detection system of claim 11, wherein the gas from the isolated source is selected from the group consisting of nitrogen, argon, and air.

13. The detection system of claim 9, wherein said purging system comprises a filter to allow filtering of the purge gas before it enters said housing.

14. The detection system of claim 9, wherein said purging system further comprises a valve for controlling the flow of the purge gas.

15. The detection system of claim 1, wherein said first optical system comprises a lens.

16. The detection system of claim 1, wherein said first optical system comprises a transparent window.

17. The detection system of claim 1, wherein said photodetector is positioned substantially orthogonal to said beam of radiation.

* * * * *